(12) United States Patent
Yasuda et al.

(10) Patent No.: US 10,252,971 B2
(45) Date of Patent: Apr. 9, 2019

(54) METHOD FOR PRODUCING HALOGENATED ACRYLIC ACID DERIVATIVE

(71) Applicant: AGC Inc., Chiyoda-ku (JP)

(72) Inventors: Arata Yasuda, Chiyoda-ku (JP); Mitsugu Kasagawa, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/055,903

(22) Filed: Feb. 29, 2016

(65) Prior Publication Data

US 2017/0057902 A1 Mar. 2, 2017

(30) Foreign Application Priority Data

Aug. 27, 2015 (JP) ................................. 2015-168339

(51) Int. Cl.
*C07C 67/00* (2006.01)
*C07C 43/313* (2006.01)
*C07C 43/32* (2006.01)
*C07C 41/50* (2006.01)
*C07C 41/54* (2006.01)

(52) U.S. Cl.
CPC .............. *C07C 67/00* (2013.01); *C07C 41/50* (2013.01); *C07C 41/54* (2013.01); *C07C 43/313* (2013.01); *C07C 43/32* (2013.01); *C07C 2601/02* (2017.05)

(58) Field of Classification Search
None
See application file for complete search history.

(56) References Cited

U.S. PATENT DOCUMENTS 4,570,018 A * 2/1986 Aoki ...................... C07C 43/192
558/250
5,767,325 A * 6/1998 Schroder ................ C07C 41/28
568/691

FOREIGN PATENT DOCUMENTS

CN 105130798 A 12/2015
EP 0 127 920 A2 12/1984
(Continued)

OTHER PUBLICATIONS

Nishitani et al. The Journal of Antibiotics, 1988, 332-342.*
(Continued)

*Primary Examiner* — Ana Z Muresan
(74) *Attorney, Agent, or Firm* — Oblon, McClelland, Maier & Neustadt, L.L.P.

(57) ABSTRACT

To provide a novel method for producing a halogenated acrylic acid derivative.
A compound represented by the formula (1):

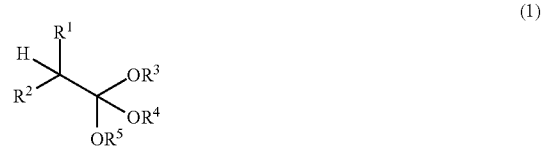

(wherein each of $R^1$ and $R^2$ which are independent of each other, is a hydrogen atom or a monovalent group essentially containing a carbon atom, or $R^1$ and $R^2$ together form a ring, $R^3$ is a monovalent group capable of being desorbed by $R^3OH$ removal reaction, and each of $R^4$ and $R^5$ which are independent of each other, is a hydrogen atom or a monovalent group essentially containing a carbon atom) and having a boiling point of at most 500° C., is subjected to $R^3OH$ removal reaction in a vapor phase in the presence of a solid catalyst to obtain an ethene derivative represented by the formula (2):

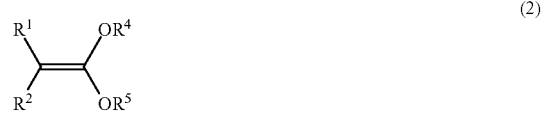

the ethene derivative represented by the formula (2) and a halogenated methane represented by the formula (3):

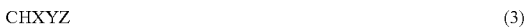

(wherein each of X, Y and Z which are independent of one another, is a halogen atom) are reacted in the presence of a basic compound and a phase transfer catalyst, to obtain a cyclopropane derivative represented by the formula (4):

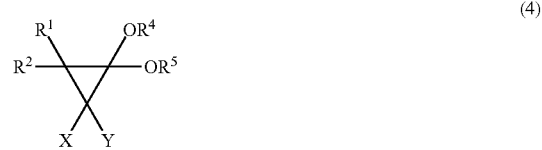

and the cyclopropane derivative represented by the formula (4) is reacted by heating in a liquid phase or in a vapor phase to obtain a halogenated acrylic acid ester derivative represented by the formula (5):

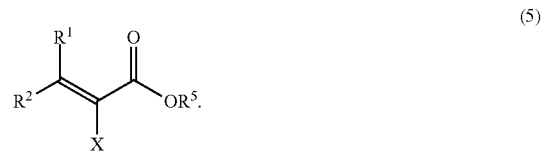

11 Claims, No Drawings

(56) References Cited

FOREIGN PATENT DOCUMENTS

| EP | 0 776 879 A1 | 6/1997 |
|----|--------------|--------|
| FR | 2 573 069 A1 | 5/1986 |
| JP | 5628305 B2 | 11/2014 |
| WO | WO 2010/149683 A1 | 12/2010 |

OTHER PUBLICATIONS

Organic Synthesis Coll.; vol. 3 and vol. 23, 1955 and 1943, 4 Pages.
S. M. McElvain et al., "Ketene Acetals. XXIII. Dealcoholation of Orthoesters with Aluminum t-Butoxide" J. Am. Chem. Soc., vol. 73, XP55291682, Jan. 1, 1951, pp. 1400-1402.
Y. Nishitani et al., "cis-Halovinylthioacetamido Side Chain, A New Effective Structural Element for 7β-Substitution in Cephem and Oxacephem Antibiotics", The Journal of Antibiotics, Mar. 1988, pp. 332-342.
F. Beyerstedt et al., "The Preparation and Properties of Ketene Diethylacetal", Journal of the American Chemical Society, Mar. 1936, 58(3), pp. 529-531.

* cited by examiner

METHOD FOR PRODUCING HALOGENATED ACRYLIC ACID DERIVATIVE

FIELD OF INVENTION

The present invention relates to a novel method for producing a halogenated acrylic acid derivative.

BACKGROUND OF INVENTION

α-Fluoroacrylic acid esters representing halogenated acrylic acid derivatives are useful as synthetic intermediates of pharmaceutical agents, polymers, optical materials, coating compositions, semiconductor resist materials, etc. and as monomers for functional polymers.

As a method for producing an α-fluoroacrylic acid ester, a method (Patent Document 1) has been known in which 3-hydroxy-2-fluoropropionic acid ester is converted to 3-chloro-2-fluoropropionic acid ester with thionyl chloride, from which hydrochloric acid is desorbed to form 2-fluoroacrylic acid ester.

Patent Document 2 discloses a process for preparing α-fluoroacrylic acid ethyl ester by converting an ethylene derivative to a cyclopropane derivative with potassium t-butoxide and a chlorofluorocarbon in large excess, and decomposing the cyclopropane derivative to produce an α-fluoroacrylic acid ethyl ester. As a method for preparing the ethylene derivative used in Patent Document 2, a method of reacting potassium t-butoxide with 1,1-diethoxy-2-bromoethane to desorb hydrobromic acid thereby to obtain 1,1-diethoxyethene has been known (Non-Patent Document 1).

PRIOR ART DOCUMENTS

Patent Documents

Patent Document 1: Japanese Patent No. 5628305
Patent Document 2: EP0127920

Non-Patent Document

Non-Patent Document 1: Organic Synthesis, Coll. Vol. 3, p. 506 (1955); Vol. 23, p. 45 (1943)

SUMMARY OF INVENTION

Technical Problem

The method disclosed in Patent Document 1 has safety problems since toxic thionyl chloride is used. Further, it is disadvantageous industrially also since corrosive hydrogen chloride is generated. Further, it is inferior in economical efficiency and productivity since $F_2$ which is expensive and which is difficult to handle is used to prepare 3-hydroxy-2-fluoropropionic acid ester as the material.

The method disclosed in Patent Document 2 also is inferior in the cost in industrial production since expensive potassium t-butoxide and a chlorofluorocarbon in large excess are used.

The method disclosed in Non-Patent Document 1 is also disadvantageous in economical efficiency and productivity since expensive potassium t-butoxide is used and in addition, highly corrosive hydrogen bromide is generated.

Under these circumstances, the object of the present invention is to provide a novel method for producing a halogenated acrylic acid derivative which achieves a high conversion ratio, a high selectivity and a high yield, and which satisfies safety and economical efficiency.

Solution to Problem

The present inventors have found very advantageous catalyst and reaction method to produce a desired halogenated acrylic acid ester derivative from inexpensive and easily available materials via a novel and useful intermediate, and accomplished the present invention.

That is, the present invention provides the following.

[1] A method for producing an ethene derivative represented by the following formula (2), which comprises subjecting a compound represented by the following formula (1) and having a boiling point of at most 500° C. to $R^3OH$ removal reaction in a vapor phase in the presence of a solid catalyst:

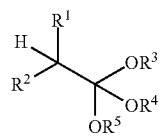

(1)

wherein each of $R^1$ and $R^2$ which are independent of each other, is a hydrogen atom or a monovalent group essentially containing a carbon atom, or $R^1$ and $R^2$ together form a ring, $R^3$ is a monovalent group capable of being desorbed by the $R^3OH$ removal reaction, and each of $R^4$ and $R^5$ which are independent of each other, is a hydrogen atom or a monovalent group essentially containing a carbon atom;

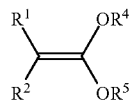

(2)

wherein $R^1$, $R^2$, $R^4$ and $R^5$ are as defined above.

[2] The method for producing an ethene derivative according to [1], wherein each of $R^1$ and $R^2$ which are independent of each other, is a hydrogen atom, an alkyl group, a cycloalkyl group, an alkoxy group, an aryl group, an aryloxy group, an alkyl group having a substituent, a cycloalkyl group having a substituent, an alkoxy group having a substituent, an aryl group having a substituent, or an aryloxy group having a substituent, and each of $R^3$, $R^4$ and $R^5$ which are independent of one another, is an alkyl group, a cycloalkyl group, an aryl group, an alkyl group having a substituent, a cycloalkyl group having a substituent, or an aryl group having a substituent.

[3] The method for producing an ethene derivative according to [1] or [2], wherein the reaction temperature is from 100 to 500° C.

[4] The method for producing an ethene derivative according to any one of [1] to [3], wherein the solid catalyst is at least one solid catalyst selected from a metal catalyst and a metal oxide catalyst.

[5] The method for producing an ethene derivative according to any one of [1] to [4], wherein the solid catalyst is a metal oxide catalyst.

[6] The method for producing an ethene derivative according to [5], wherein the metal oxide catalyst is a catalyst containing at least one member selected from the group consisting of zirconia, alumina, zeolite and zinc oxide.

[7] A method for producing a cyclopropane derivatives represented by the following formula (4), which comprises producing the ethene derivative represented by the above formula (2) by the production method as defined in any one of [1] to [6], and reacting the ethene derivative and a compound represented by the following formula (3) in the presence of a basic compound and a phase transfer catalyst:

CHXYZ (3)

wherein each of X, Y and Z which are independent of one another, is a halogen atom.

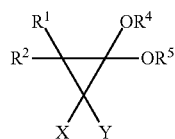

(4)

wherein $R^1$, $R^2$, $R^4$, $R^5$, X and Y are as defined above.

[8] The method for producing a cyclopropane derivative according to [7], wherein the basic compound is at least one member selected from the group consisting of an alkali metal hydroxide, an alkali metal alkoxide, an alkali metal hydride and an alkyllithium.

[9] The method for producing a cyclopropane derivative according to [7] or [8], wherein the phase transfer catalyst is a quaternary ammonium salt.

[10] The method for producing a cyclopropane derivative according to any one of [7] to [9], wherein X is a fluorine atom, and Y is a chlorine atom or a fluorine atom.

[11] A method for producing a halogenated acrylic acid ester derivative represented by the following formula (5), which comprises producing the cyclopropane derivative represented by the above formula (4) by the production method as defined in any one of [7] to [10], and subjecting the cyclopropane derivative to $R^4Y$ removal reaction by heating it in a liquid phase or in a vapor phase:

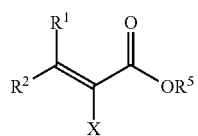

(5)

wherein $R^1$, $R^2$, $R^5$ and X are as defined above.

[12] The method for producing a halogenated acrylic acid ester derivative according to [11], wherein X is a fluorine atom.

[13] The method for producing a halogenated acrylic acid ester derivative according to [11] or [12], wherein the temperature of the $R^4Y$ removal reaction is from 80 to 400° C.

[14] A method for producing a halogenated acrylic acid ester derivative represented by the following formula (5), which comprises producing the cyclopropane derivative represented by the above formula (4) and a propene derivative represented by the following formula (8) by the production method as defined in any one of [7] to [10], separating the cyclopropane derivative and the propene derivative, and decomposing the separated propene derivative under acidic conditions:

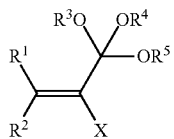

(8)

wherein each of $R^1$ and $R^2$ which are independent of each other, is a hydrogen atom or a monovalent group essentially containing a carbon atom, $R^3$ is a monovalent group capable of being desorbed by the $R^3OH$ removal reaction, and each of $R^4$ and $R^5$ which are independent of each other, is a hydrogen atom or a monovalent group essentially containing a carbon atom;

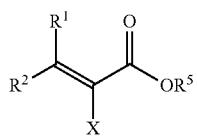

(5)

wherein $R^1$, $R^2$, $R^5$ and X are as defined above.

[15] The method for producing a halogenated acrylic acid ester derivative according to any one of [11] to [14], wherein production of the halogenated acrylic acid ester derivative represented by the formula (5) is carried out in the presence of a polymerization inhibitor.

[16] The method for producing a halogenated acrylic acid ester derivative according to [15], wherein the amount of the polymerization inhibitor is at least 10 ppm based on the halogenated acrylic acid ester derivative.

[17] A compound represented by the following formula (6):

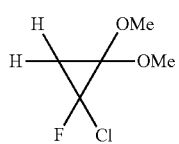

(6)

wherein Me is a methyl group.

[18] A compound represented by the following formula (7):

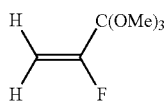

(7)

wherein Me is a methyl group.

Advantageous Effects of Invention

According to the present invention, it is possible to obtain a desired halogenated acrylic acid ester derivative from an inexpensive and easily available material via a novel and useful intermediate with a high conversion ratio, a high selectivity and a high yield.

DETAILED DESCRIPTION OF INVENTION

Terms in this specification are defined as follows.

An "alkyl group" means a linear or branched monovalent saturated hydrocarbon group. The number of carbon atoms in the alkyl group is preferably from 1 to 20, more preferably from 1 to 15, further preferably from 1 to 12, particularly preferably from 1 to 6. The alkyl group may, for example, be a methyl group, an ethyl group, a n-propyl group, an isopropyl group, a n-butyl group, an isobutyl group, a sec-butyl group, a tert-butyl group, a n-pentyl group, an isopentyl group, a neopentyl group, a tert-pentyl group, a 1-ethylpropyl group, a n-hexyl group, an isohexyl group or a neohexyl group.

The "alkyl group" may be a monovalent saturated hydrocarbon group partially having a cyclic structure. It may, for example, be a cycloalkylalkyl group.

A "cycloalkyl group" means a cyclic monovalent saturated hydrocarbon group. The number of carbon atoms in the cycloalkyl group is preferably from 3 to 20, more preferably from 3 to 15, further preferably from 3 to 12, particularly preferably from 3 to 6. The number of the cyclic structure in the cycloalkyl group may be one or more. In a case where the cycloalkyl group has two or more cyclic structures, it may be a group having a condensed polycyclic structure, a bridged cyclic structure or a spirocyclic structure. The cycloalkyl group may, for example, be a cyclopropyl group, a cyclobutyl group, a cyclopentyl group or a cyclohexyl group.

An "alkenyl group" means a group having an optional carbon-carbon single bond in the above alkyl group (excluding a methyl group) converted to a carbon-carbon double bond. The number of carbon atoms in the alkenyl group is preferably from 2 to 20, more preferably from 2 to 15, further preferably from 2 to 12, particularly preferably from 2 to 6. The alkenyl group may, for example, be an ethenyl group, a 1-propenyl group, a 2-propenyl group, a 1-methyl-1-ethenyl group, a 1-butenyl group, a 2-butenyl group, a 3-butenyl group, a 2-methyl-1-propenyl group, a 2-methyl-2-propenyl group, a 1-ethylethenyl group, a 1-methyl-1-propenyl group, a 1-methyl-2-propenyl group, a 1-pentenyl group or a 1-hexenyl group.

A "cycloalkenyl group" means a group having an optional carbon-carbon single bond in the above cycloalkyl group converted to a carbon-carbon double bond. The number of the cyclic structure in the cycloalkenyl group may be one or more. In a case where the cycloalkenyl group has two or more cyclic structures, it may be a group having a condensed polycyclic structure, a bridged cyclic structure or a spirocyclic structure. The number of carbon atoms in the cycloalkenyl group is from 3 to 20, preferably from 3 to 15, more preferably from 3 to 12, further preferably from 3 to 6. The cycloalkenyl group may, for example, be a 1-cyclopentenyl group, a 2-cyclopentenyl group, a 3-cyclopentenyl group, a 1-methyl-2-cyclopentenyl group, a 1-cyclohexenyl group, a 2-cyclohexenyl group or a 3-cyclohexenyl group.

An "alkynyl group" means a group having an optional carbon-carbon single bond in the above alkyl group (excluding a methyl group) converted to a carbon-carbon triple bond. The number of carbon atoms in the alkynyl group is preferably from 2 to 20, more preferably from 2 to 15, further preferably from 2 to 12, particularly preferably from 2 to 6. The alkynyl group may, for example, be an ethynyl group, a 1-propynyl group, a 2-propynyl group, a 1-butynyl group, a 2-butynyl group, a 3-butynyl group, a 1-methyl-2-propynyl group, a 1-pentynyl group or a 1-hexynyl group.

An "alkoxy group" means a group having an etheric oxygen atom (—O—) bonded to the terminal carbon atom of an alkyl group. The alkoxy group is preferably linear or branched. The number of carbon atoms in the alkoxy group is preferably from 1 to 20, more preferably from 1 to 15, further preferably from 1 to 12, particularly preferably from 1 to 6. The alkoxy group may, for example, be a methoxy group, an ethoxy group, a n-propoxy group, an isopropoxy group, a n-butoxy group, an isobutoxy group, a sec-butoxy group, a tert-butoxy group, a n-pentyloxy group or a n-hexyloxy group.

An "aryl group" means a monocyclic, bicyclic or higher aromatic hydrocarbon group. The number of carbon atoms in the aryl group is preferably from 6 to 22, more preferably from 6 to 18, further preferably from 6 to 14, particularly preferably from 6 to 10. The aryl group may, for example, be a phenyl group, an o-, p- or m-tolyl group, a naphthyl group, a phenanthrenyl group, an anthracenyl group or a fluorenyl group.

A "heteroaryl group" means an aromatic group containing at least one hetero atom. The hetero atom is preferably an oxygen atom, a sulfur atom or a nitrogen atom. The number of carbon atoms in the heteroaryl group is from 3 to 21, preferably from 3 to 17, more preferably from 3 to 13, further preferably from 3 to 9. The heteroaryl group may, for example, be a pyridyl group, a pyrimidinyl group, a pyridazinyl group, a pyrazinyl group, a thienyl group, a furyl group, a pyrrolyl group, a pyrazolyl group, a triazolyl group, an imidazolyl group, a thiazolyl group, an oxazolyl group, an indolyl group or a quinolyl group.

An "aryloxy group" means a group having an etheric oxygen atom (—O—) bonded to the terminal of the above aryl group. The number of carbon atoms in the aryloxy group is preferably from 7 to 23, more preferably from 7 to 19, further preferably from 7 to 15, particularly preferably from 7 to 11. The aryloxy group may, for example, be a phenoxy group.

An "alkylthio group" means a group having the above alkyl group bonded via a sulfur atom. The number of carbon atoms in the alkylthio group is preferably from 1 to 20, more preferably from 1 to 15, further preferably from 1 to 12, particularly preferably from 1 to 6. The alkylthio group may, for example, be a methanethio group, an ethanethio group, a n-propanethio group, an isopropanethio group, a n-butanethio group, an isobutanethio group, a s-butanethio group, a t-butanethio group, a n-pentanethio group or a n-hexanethio group.

A "monoalkylamino group" means a group having one hydrogen atom in an amino group (—NH$_2$) substituted by the above alkyl group. A "dialkylamino group" means two hydrogen atoms in an amino group substituted by the above alkyl groups. The number of carbon atoms in the monoalkylamino group is preferably from 1 to 20, more preferably from 1 to 15, further preferably from 1 to 12, particularly preferably from 1 to 8. The number of carbon atoms in the dialkylamino group is preferably from 2 to 20, more preferably from 2 to 15, further preferably from 2 to 12, particularly preferably from 2 to 8. The monoalkylamino group may, for example, be a methylamino group, an ethylamino group, a n-propylamino group, an isopropylamino group, a t-butylamino group, a n-pentylamino group or a n-hexylamino group. The dialkylamino group may, for example, be a N,N-dimethylamino group or a N,N-diethylamino group.

A "monoarylamino group" means a group having one hydrogen atom in an amino group substituted by the above aryl group. A "diarylamino group" means a group having two hydrogen atoms in an amino group substituted by the above aryl groups. The number of carbon atoms in the monoarylamino group is preferably from 6 to 22, more preferably from 6 to 18, further preferably from 6 to 14, particularly preferably from 6 to 10. The number of carbon atoms in the diarylamino group is preferably from 12 to 24, more preferably from 12 to 20, further preferably from 12 to 16. The monoarylamino group may, for example, be a phenylamino group, and the diarylamino group may, for example, be a diphenylamino group.

A "heterocyclyl group" means a saturated or unsaturated monovalent heterocyclic group containing at least one hetero atom. The hetero atom is preferably an oxygen atom, a sulfur atom or a nitrogen atom. The number of carbon atoms in the heterocyclyl group is preferably from 3 to 21, more preferably from 3 to 17, further preferably from 3 to 13, particularly preferably from 3 to 9. The heterocyclyl group may, for example, be an azepanyl group, a pyrrolidinyl group, a piperidinyl group, a piperazinyl group, a morpholinyl group or a tetrahydrofuryl group.

A "halogen atom" is preferably a fluorine atom, a chlorine atom, a bromine atom or an iodine atom, particularly preferably a fluorine atom or a chlorine atom.

The hydrogen atom bonded to a carbon atom in each of the above groups may be substituted by a substituent. Such a group substituted by a substituent will be referred to as a group having a substituent. The substituent may, for example, be an alkyl group, an alkenyl group, an alkoxy group, an aryl group, an alkylthio group, a nitro group, an amino group, a carboxy group, a cycloalkyl group, a hydroxy group, a halogen atom, a cyano group, a phenyl group or a heterocyclyl group.

Now, the production method of the present invention will be described in detail below. The concept of the production method of the present invention is represented as follows.

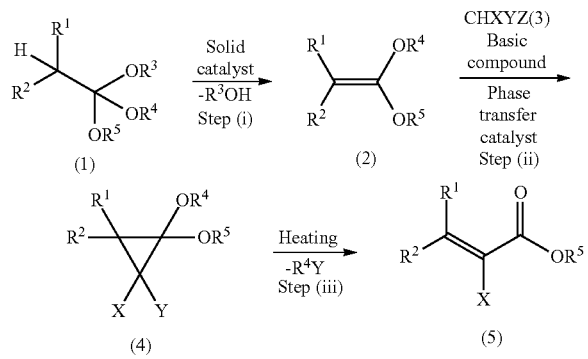

[Step (i)]

The step (i) is a step of subjecting a compound represented by the above formula (1) and having a boiling point of at most 500° C. (hereinafter sometimes referred to as an "orthocarboxylic acid ester (1)") to $R^3OH$ removal reaction in a vapor phase in the presence of a solid catalyst to produce an ethene derivative represented by the above formula (2) (hereinafter sometimes referred to simply as an "ethene derivative (2)").

In the orthocarboxylic acid ester (1) as a material in the step (i), each of $R^1$ and $R^2$ which are independent of each other, is a hydrogen atom or a monovalent group essentially containing a carbon atom.

Specifically, each of $R^1$ and $R^2$ which are independent of each other, is preferably a hydrogen atom, an alkyl group, a cycloalkyl group, an alkenyl group, a cycloalkenyl group, an alkynyl group, an alkoxy group, an aryl group, a heteroaryl group, an aryloxy group, an arylalkyl group, an alkylthio group, a monoalkylamino group, a dialkylamino group, a monoarylamino group, a diarylamino group, a heterocyclyl group, an alkyl group having a substituent, a cycloalkyl group having a substituent, an alkenyl group having a substituent, a cycloalkenyl group having a substituent, an alkynyl group having a substituent, an alkoxy group having a substituent, an aryl group having a substituent, a heteroaryl group having a substituent, an aryloxy group having a substituent, an arylalkyl group having a substituent, an alkylthio group having a substituent, a monoalkylamino group having a substituent, a dialkylamino group having a substituent, a monoarylamino group having a substituent, a diarylamino group having a substituent or a heterocyclyl group having a substituent. Each of $R^1$ and $R^2$ which are independent of each other, is more preferably a hydrogen atom, an alkyl group, a cycloalkyl group, an alkoxy group, an aryl group, an aryloxy group, an alkyl group having a substituent, a cycloalkyl group having a substituent, an alkoxy group having a substituent or an aryl group having a substituent.

Otherwise, $R^1$ and $R^2$ together may form a ring. In a case where $R^1$ and $R^2$ form a ring, for example, $R^1$ and $R^2$ form, together with the carbon atom to which they are bonded, a cycloalkyl group such as a cyclohexyl group or a cycloalkyl group having a substituent, such as a cyclohexyl group substituted by an alkyl group.

$R^3$ is a monovalent group capable of being desorbed by $R^3OH$ removal reaction. $R^3$ is specifically preferably an alkyl group, a cycloalkyl group, an alkenyl group, a cycloalkenyl group, an alkynyl group, an aryl group, a heteroaryl group, a heterocyclyl group, an alkyl group having a substituent, a cycloalkyl group having a substituent, an alkenyl group having a substituent, a cycloalkenyl group having a substituent, an alkynyl group having a substituent, an aryl group having a substituent, a heteroaryl group having a substituent, an arylalkyl group having a substituent or a heterocyclyl group having a substituent.

$R^3$ is more preferably an alkyl group, a cycloalkyl group, an aryl group, an alkyl group having a substituent, a cycloalkyl group having a substituent or an aryl group having a substituent.

Each of $R^4$ and $R^5$ which are independent of each other, is a hydrogen atom or a monovalent group essentially containing a carbon atom, and is specifically preferably a hydrogen atom, an alkyl group, a cycloalkyl group, an alkenyl group, a cycloalkenyl group, an alkynyl group, an aryl group, a heteroaryl group, a heterocyclyl group, an alkyl group having a substituent, a cycloalkyl group having a substituent, an alkenyl group having a substituent, a cycloalkenyl group having a substituent, an alkynyl group having a substituent, an aryl group having a substituent, a heteroaryl group having a substituent, an arylalkyl group having a substituent or a heterocyclyl group having a substituent. Each of $R^4$ and $R^5$ is more preferably an alkyl group, a cycloalkyl group, an aryl group, an alkyl group having a substituent, a cycloalkyl group having a substituent or an aryl group having a substituent.

The substituent in the orthocarboxylic acid ester (1) should be selected so that the boiling point of the orthocarboxylic acid ester (1) is within the above range.

The orthocarboxylic acid ester (1) may be prepared by a known method or similar method in accordance with a conventional method in organic chemistry. Trimethyl orthoacetate which is a representative example is commercially available and is very easily available.

Since the reaction of the step (i) is carried out in a vapor phase, the boiling point of the orthocarboxylic acid ester (1) is preferably a temperature at which the orthocarboxylic acid ester (1) vaporizes at the reaction temperature under the reaction pressure. The boiling point hereinafter means a boiling point at 1 atm (absolute pressure).

The boiling point of the orthocarboxylic acid ester (1) is at most 500° C., preferably at most 450° C., more preferably at most 400° C. Further, the boiling point of the orthocarboxylic acid ester (1) is preferably at least 0° C., more preferably at least 20° C., further preferably at least 50° C. in view of handling efficiency.

The solid catalyst used in the reaction of the step (i) is selected from catalysts which accelerate the $R^3OH$ removal reaction of the compound represented by the formula (1).

The solid catalyst may, for example, be a metal catalyst, a metal oxide catalyst, a natural mineral, a molecular sieve or carbon black. The natural mineral is preferably acid clay, kaolinite, bentonite, montmorillonite, talc, zirconium silicate, zeolite or the like. Among them, the solid catalyst is preferably at least one member selected from a metal catalyst and a metal oxide catalyst, more preferably a metal oxide catalyst.

The metal catalyst is preferably a catalyst consisting of a metal of Group IVB or Group VIII of the Periodic Table, and is preferably molybdenum, tungsten, chromium, iron, cobalt, nickel, platinum, palladium, iridium, osmium, rhodium, rhenium or ruthenium.

The metal oxide catalyst means a catalyst containing a metal oxide, and is preferably silica, alumina, zirconia, titania, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, zeolite or a mixture thereof. The metal oxide catalyst may be silica-alumina, silica-magnesia, silica-boria, alumina-boria, silica-titania or silica-zirconia in an optional molar ratio, or a composite metal oxide with a molecular sieve or the like, or a mixture thereof.

The metal oxide catalyst is more preferably a catalyst containing at least one member selected from the group consisting of zirconia, alumina, zeolite and zinc oxide. In such a case, the content of at least one metal oxide selected from the group consisting of zirconia, alumina and zinc oxide in the metal oxide catalyst is preferably at least 50 mass %, more preferably at least 60 mass %, further preferably at least 70 mass % based on the metal oxide catalyst.

Among the metal oxides, zeolite is preferably zeolite A, zeolite L, zeolite X, zeolite Y, zeolite MFI represented by ZSM-5, zeolite MWW, zeolite β, mordenite, ferrierite or erionite.

Other solid catalyst used for the reaction of the step (i) may, for example, be a solid catalyst such as chlorinated alumina, fluorinated alumina or metallosilicate catalyst, or a solid catalyst having a phosphorus compound, a boron compound or the like supported on an inert carrier.

In the reaction of the step (i), the solid catalysts may be used alone or in combination of two or more.

The reaction of the step (i) is carried out in a vapor phase. The reaction in a vapor phase may be carried out by a conventional vapor phase flow method. The vapor phase flow method is a method in which a reactor is packed with a solid catalyst, and a vaporized material is made to flow through a catalyst layer for reaction. Specifically, a reaction method such as a fixed bed flow method, a fixed bed circulation method or a fluidized bed flow method may be mentioned, and in the present invention, any of these reaction methods may be applicable.

For example, in the vapor phase flow method, a vaporized material is made to flow through the catalyst layer, and the material may be made to flow alone or together with a carrier gas. The carrier gas is not particularly limited, and is preferably an inert gas such as a nitrogen gas, a helium gas or an argon gas or a mixture thereof. In a case where the carrier gas is used, the amount of the carrier gas is preferably more than 0 and at most 20 molar equivalent, more preferably more than 0 and at most 10 molar equivalent per 1 mol of the orthocarboxylic acid ester (1).

The reaction pressure is not particularly limited, and the reaction may be carried out under elevated pressure, normal pressure or reduced pressure. The reaction pressure is preferably from normal pressure to slightly elevated pressure, whereby the operation will easy.

If desired, a filling material such as a static mixer or Raschig rings may be used. The method of heating the reactor is not particularly limited, and preferred is a method of heating by a heat transfer oil, a fused salt, an electric heater or sand. The reaction temperature in the step (i) is preferably from 100 to 500° C., more preferably from 120 to 450° C., further preferably from 150 to 400° C.

The reaction time in the step (i) corresponds to a time over which the orthocarboxylic acid ester (1) is in contact with the solid catalyst (hereinafter referred to as "contact time"). The contact time is preferably from 0.1 to 60 seconds, more preferably from 1 to 30 seconds. In general, if the contact time is short, the conversion ratio tends to decrease, and if it is long, by-products tend to form, or impurities such as a carbide are attached to the catalyst surface to lower the catalytic activity. The optimum contact time depends on the reaction temperature. For example, if the reaction temperature is 100° C. and the contact time is extremely short, the reaction may not substantially proceed in some cases, and if the reaction temperature is 500° C. and the contact time is extremely long, by-products may form, or tar or oil may form thereby to clog the reactor.

The step (i) is a step of carrying out production of the ethene derivative (2) which has been difficult, by a vapor phase reaction which is very advantageous in view of handling efficiency and productivity, by use of a solid catalyst.

Since the reaction of the step (i) is a vapor phase reaction, production can be continuously carried out for example by a reaction method such that the material is made to flow through a tubular reactor, and the reaction of the step (i) is very excellent in productivity as compared with a conventional batch production method. Further, since the reaction is carried out in a vapor phase, the formed product can be very easily separated. Further, the step (i) is highly safely carried out, is less limited in the reaction apparatus and is industrially very advantageous since highly corrosive hydrogen chloride or the like will not form.

By the reaction of the step (i) of the present invention, an ethene derivative (2) wherein $R^4$ and $R^5$ are methyl, which has been difficult to produce industrially and economically by a conventional method, can be easily obtained with a high yield.

The ethene derivative (2) obtained in the step (i) is useful as a synthetic intermediate of various chemical products. In the present invention, the following step (ii) is preferably carried out using the obtained ethene derivative (2) to obtain the desired halogenated acrylic acid ester.

[Step (ii)]

The step (ii) is a step of reacting the ethene derivative (2) obtained in the step (i) with a halogenated methane represented by the above formula (3) (hereinafter sometimes referred to simply as a "halogenated methane (3)") in the presence of a basic compound and a phase transfer catalyst to produce a cyclopropane derivative represented by the above formula (4) (hereinafter sometimes referred to simply as a "cyclopropane derivative (4)").

The ethene derivative (2) obtained in the step (i) may be used for the reaction of the step (ii) as it is without purification, or may be used after purification. The purification method may, for example, be a known method such as extraction with a solvent, distillation or crystallization. In the purification, unreacted orthocarboxylic acid ester (1) contained in the product in the step (i) may be separated and recycled in the step (i), whereby the productivity will further improve.

In the reaction of the step (ii), the halogenated methane (3) used is considered to form a carbene by the action of the basic compound and be inserted to the double bond of the ethene derivative (2).

The halogenated methane (3) may, for example, be preferably chloroform, dichlorofluoromethane, chlorodifluoromethane or trifluoromethane.

The amount of the halogenated methane (3) used is preferably at least 1 molar time, particularly preferably from 1 to 5 molar times, especially preferably from 1 to 2 molar times per mole of the ethene derivative (2).

The basic compound used in the reaction of the step (ii) is a compound which accelerates a reaction to form a carbene from the halogenated methane (3).

The basic compound is preferably a hydroxide of an alkaline earth metal or an alkali metal such as sodium hydroxide or potassium hydroxide; a metal alkoxide such as sodium methoxide, sodium ethoxide or potassium t-butoxide; a metal hydride such as sodium hydride; an alkyllithium compound such as butyllithium; a metal carbonate such as sodium carbonate or potassium carbonate; or a metal hydrogen phosphate or a metal phosphate such as sodium phosphate, potassium phosphate, sodium hydrogen phosphate or potassium hydrogen phosphate. The basic compound is more preferably a hydroxide of an alkali metal or an alkaline earth metal, a metal alkoxide, a metal carbonate, a metal hydrogen phosphate, a metal phosphate or a metal hydride. The basic compound is further preferably a hydroxide of an alkali metal or an alkaline earth metal. Such basic compounds may be used alone or in combination of two or more.

The amount of the basic compound used for the reaction of the step (ii) is an amount such that a carbene in a sufficient amount for the reaction with the ethene compound is formed from the halogenated methane (3), and is preferably from 1 to 10 molar times, more preferably from 1 to 8 molar times, further preferably from 1 to 6 molar times per mole of the halogenated methane (3).

The reaction of the step (ii) is carried out in the presence of a phase transfer catalyst together with the basic compound. The phase transfer catalyst is preferably a compound represented by the formula $(R^a)_4M^+A^-$ (wherein $R^a$ is independently a hydrogen atom or a $C_{1-25}$ hydrocarbon, M is N or P, and A is OH, F, Br, Cl, I, $HSO_4$, CN, $CH_3SO_3$ or $PhCH_2CO_2$, and Ph is a phenyl group). Specifically, it may, for example, be a salt having an alkylammonium cation such as a tetrabutylammonium salt, a trioctylmethylammonium salt or a benzyldimethyloctadecylammonium salt, or a crown ether. The alkyl group is preferably a $C_{1-25}$ linear alkyl group, more preferably a $C_{1-20}$ linear alkyl group. The phase transfer catalyst is preferably a quaternary ammonium salt such as tetrabutylammonium bromide or tetrabutylammonium chloride.

The phase transfer catalyst may be used as a catalyst between phases of an aqueous phase and an organic phase, or may be used as a catalyst between two organic phases which are separated, e.g. a chlorofluorohydrocarbon solvent and a hydrocarbon solvent.

The reaction of the step (ii) is carried out in a liquid phase preferably in the presence of a solvent.

The solvent is preferably water, an aliphatic hydrocarbon, a halogenated aliphatic hydrocarbon, an aromatic hydrocarbon or a halogenated aromatic hydrocarbon. Examples of a preferred solvent include benzene, toluene, xylene, monochlorobenzene, dichlorobenzene, trichlorobenzene, petroleum ethers, pentane, hexane, cyclohexane, heptane, octane, nonane, decane, undecane, dodecane, tridecane, tetradecane, dichloromethane, chloroform and carbon tetrachloride. Such solvents may be used alone or in combination of two or more.

The amount of the solvent is preferably from 10 to 1,000 vol %, more preferably from 50 to 800 vol % per 100 vol % of the ethene derivative (2).

In the step (ii), the order of introduction of the ethene derivative (2), the halogenated methane (3), the basic compound and the phase transfer catalyst into the reactor is not particularly limited. They may be introduced simultaneously into the reactor and mixed, or the basic compound and the phase transfer catalyst are mixed in the rector and then the ethene derivative (2) and the halogenated methane (3) are sequentially or simultaneously introduced.

The reaction temperature of the step (ii) is preferably from −20° C. to +50° C., more preferably from −0° C. to +40° C., further preferably from 0° C. to +30° C. The reaction pressure is not particularly limited, and the reaction may be carried out under any of elevated pressure, normal pressure and reduced pressure.

In the step (ii), in addition to the cyclopropane derivative (4), a compound represented by the following formula (8) (hereinafter sometimes referred to as a "propene derivative (8)") forms.

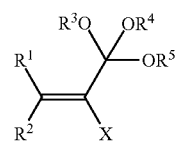

(8)

wherein each of $R^1$ and $R^2$ which are independent of each other, is a hydrogen atom or a monovalent group essentially containing a carbon atom, $R^3$ is a monovalent group capable of being desorbed by the $R^3OH$ removal reaction, and each of $R^4$ and $R^5$ which are independent of each other, is a hydrogen atom or a monovalent group essentially containing a carbon atom.

The propene derivative (8) may be converted to an α-halogenated acrylic acid ester which is a product of the after-mentioned step (iii) by decomposition under acidic conditions in the presence of a solvent. Accordingly, the propene derivative (8) may be recovered to produce the halogenated acrylic acid ester, whereby the yield and the productivity can be improved.

The reaction of decomposing the propene derivative (8) is preferably carried out under acidic conditions, preferably at a pH of from 0 to 7, more preferably at a pH of from 0 to 5. The acidic conditions are preferably achieved by addition of an acid such as hydrochloric acid or sulfuric acid to the reaction system. The solvent used for the decomposition reaction is preferably an alcohol such as methanol or ethanol. Further, the amount of the solvent is preferably from 10 to 1,000 vol %, more preferably from 20 to 800 vol % per 100 vol % of the propene derivative (8). The reaction temperature is preferably from −20 to +100° C., more preferably from −10 to +80° C.

As a preferred propene derivative (8), for example, a compound represented by the following formula (7) may be mentioned.

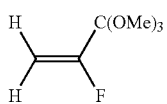
(7)

The cyclopropane derivative (4) obtained in the step (ii) is useful as an intermediate of pharmaceutical agents, polymers, etc. Particularly, a cyclopropane derivative (4) wherein X is a fluorine atom and Y is a chlorine atom or a fluorine atom is useful.

The cyclopropane derivative (4) may, for example, be a compound represented by the following formula (6). Here, Me represents a methyl group (the same applies hereinafter).

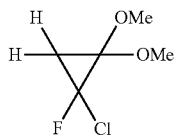
(6)

[Step (iii)]

The step (iii) is a step of subjecting the cyclopropane derivative (4) represented by the formula (4) to $R^4Y$ removal reaction by heating it in a liquid phase or a vapor phase to produce a halogenated acrylic acid ester derivative represented by the formula (5) (hereinafter sometimes referred to simply as a "halogenated acrylic acid ester derivative (5)").

The cyclopropane derivative (4) obtained in the step (ii) may be used for the reaction of the step (iii) as it is without purification or may be used after purification. The method for purifying the cyclopropane derivative (4) may be a known method such as extraction with a solvent, distillation or crystallization. At the time of purification, the unreacted ethene derivative (2) and halogenated methane (3) contained in the cyclopropane derivative (4) obtained in the step (ii) may be separated and recycled for the step (ii).

In the step (iii), the cyclopropane derivative (4) obtained in the step (ii) is heated in a reactor. The reaction of the step (iii) is a desorption reaction, and a compound represented by the formula $R^4Y$ is desorbed. The reaction of the step (iii) may be carried out in a vapor phase or in a liquid phase. The reaction temperature of the step (iii) is preferably from 80° C. to 400° C., more preferably from 100° C. to 350° C., further preferably from 120° C. to 300° C. The reaction pressure is not particularly limited, and the reaction may be carried out under any of elevated pressure, normal pressure and reduced pressure.

In a case where the reaction of the step (iii) is carried out in a liquid phase, it may be carried out in the presence or absence of a solvent, and is preferably carried out in the presence of a solvent. In a case where a solvent is used in the step (iii), the solvent is preferably a solvent stable against heat and inert to the reaction of the step (iii). The solvent may, for example, be preferably an aromatic hydrocarbon solvent such as benzene, toluene or xylene; a halogenated aromatic hydrocarbon solvent such as monochlorobenzene, dichlorobenzene or trichlorobenzene, a hydrocarbon solvent such as cyclohexane, heptane, octane, nonane, decane, undecane, dodecane, tridecane or tetradecane; an alcohol solvent such as methanol, ethanol or propanol; or a halogenated hydrocarbon solvent such as chloroform or carbon tetrachloride.

The amount of the solvent is preferably from 0 to 1,000 vol %, more preferably from 0 to 800 vol % per 100 vol % of the cyclopropane derivative (4).

The halogenated acrylic acid ester derivative (5) obtained in the step (iii) may be purified by a known method such as extraction with a solvent, distillation or crystallization.

Further, the halogenated acrylic acid ester derivative (5) obtained in the step (iii) may contain a compound which is easily polymerized to form a polymer during the reaction of the step (iii) or after isolation and purification, depending on the structure. In such a case, it is preferred to prevent polymerization during the reaction of the step (iii) or after isolation and purification by addition of a polymerization inhibitor.

The polymerization inhibitor is preferably 2,2,6,6-tetramethylpiperidine N-oxyl, p-benzoquinone, hydroquinone, hydroquinone monomethyl ether, 2,6-di-tert-butyl-4-methylphenol (BHT), 4-tert-butyl catechol, tert-butylhydroquinone, 2,5-di-tert-butylhydroquinone, 1,2,4-trihydroxybenzene, leucoquinizarin, chloranil, phenothiazine, Q-1300, Q-1301, tetraethylthiuram disulfide, sulfur or the like, more preferably hydroquinone, 2,6-di-tert-butyl-4-methylphenol (BHT) or phenothiazine. Such polymerization inhibitors may be used alone or in combination of two or more.

The amount of the polymerization inhibitor is at least 10 ppm, preferably from 20 to 50,000 ppm based on the halogenated acrylic acid ester derivative (5) obtained in the step (iii).

Addition of the polymerization inhibitor is not particularly limited, and it is preferred that the polymerization inhibitor is present in a system in which the halogenated acrylic acid ester derivative (5) is present. Specifically, it is preferred that the polymerization inhibitor is present in the reaction system, in a container at the time of purification by distillation, in the halogenated acrylic acid ester derivative (5) after purification by distillation, or the like. Further, at the time of purification by distillation, by combination of the polymerization inhibitor and aeration, self-polymerization of the halogenated acrylic acid ester derivative (5) in a vapor phase may also be effectively suppressed. The amount of oxygen introduced in aeration during distillation is not particularly limited and is an amount such that an explosion will not induced including the entire system of distillation.

The halogenated acrylic acid ester derivative (5) is useful as materials of pharmaceutical agents, polymers, optical materials, coating compositions, semiconductor resist materials, etc. Particularly, α-fluoroacrylic acid derivatives are useful, and among them, methyl α-fluoroacrylate is used for pharmaceutical agents and is very useful as a base material of polymers and optical materials.

Such a halogenated acrylic acid ester derivative (5) may, for example, be a compound represented by the following formula (9):

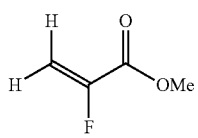
(9)

The above steps (i) to (iii) may be carried out separately, however, it is industrially advantageous to conduct these steps continuously. For example, they may be conducted as a continuous process such that the step (i) is carried out in a vapor phase, the formed product is cooled and subjected to the step (ii) in a liquid phase without purification, and the formed product in the step (ii) is heated without purification and subjected to the step (iii). By conducting such a continuous process and further conducting the above-described step of separating an unreacted product and recycling it in the previous step, the productivity will more improve.

The steps (i) to (iii) of the present invention are preferably carried out using the following reaction substrates. Intermediates and final products obtained in the respective steps are useful compounds as an intermediate of pharmaceutical agents, polymers, etc.

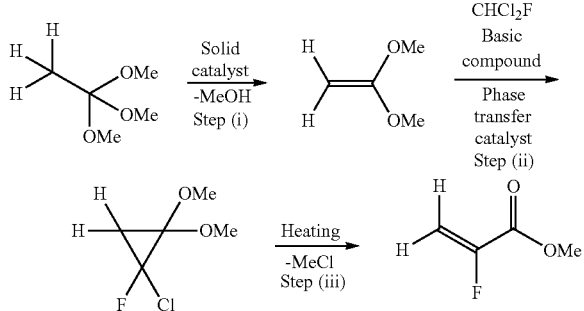

EXAMPLES

Now, the present invention will be described in further detail with reference to Examples. However, it should be understood that the present invention is by no means restricted thereto.

Examples 1 to 3

Preparation of Catalyst

A SUS316 reaction tube having an internal diameter of 15 mm and a length of 300 mm was packed with a cylindrical zinc oxide (specific surface area: 39 m²/g, "N748" manufactured by JGC Catalysts and Chemicals Ltd.) catalyst having a diameter of 4.8 mm and a length of 9.8 mm, and equipped with an electric heater. The reaction tube was heated so that the temperature of the catalyst layer would be 250° C., and nitrogen was made to flow for 3 hours to dry the catalyst.
<Step (i)>
The reaction tube was heated by the electric heater so that the temperature of the catalyst layer would be as identified in Table 1, and the reaction was carried out by flowing trimethyl orthoacetate as a material under the conditions shown in Table 1. The crude liquid discharged from the outlet of the reaction tube was collected by a cold trap at 0° C. and analyzed by gas chromatography to conduct composition analysis of the reaction product. The results are shown in Table 1.

TABLE 1

|  | Example 1 | Example 2 | Example 3 |
| --- | --- | --- | --- |
| Reaction temperature (° C.) | 250 | 300 | 350 |
| Material supply ratio (molar ratio) (Trimethyl orthoacetate/N2) | 1/2 | 1/2 | 1/2 |
| Contact time (sec) | 5 | 5 | 5 |
| Trimethyl orthoacetate conversion ratio (%) | 33.9 | 61.5 | 72.1 |
| 1,1-Dimethoxyethene selectivity (%) | 84.7 | 84.0 | 64.4 |

Further, by distillation under normal pressure using a packed column, 1,1-dimethoxyethene is obtained as a colorless liquid.

$^1$H-NMR data of 1,1-dimethoxyethene are shown below.

$^1$H-NMR (400 MHz, CDCl$_3$), δ ppm; 2.91 (s, 2H), 3.41 (s, 6H)

Examples 4 to 6

The same operation as in Example 2 was carried out except for the catalyst. The results are shown in Table 2.

TABLE 2

|  | Example 4 | Example 5 | Example 6 |
| --- | --- | --- | --- |
| Catalyst | Catalyst 1 | Catalyst 2 | Catalyst 3 |
| Trimethyl orthoacetate conversion ratio (%) | 19.1 | 30.6 | 52.2 |
| 1,1-Dimethoxyethene selectivity (%) | 77.1 | 68.1 | 61.7 |

Catalyst 1: spherical α-alumina ("HD ball" manufactured by Nikkato)
Catalyst 2: cylindrical γ-alumina ("Selexsorb COS" manufactured by N.E. CHEMCAT CORPORATION)
Catalyst 3: 5% zinc oxide-zirconium oxide (manufactured by N.E. CHEMCAT CORPORATION)

Example 7 (Step (ii))

In a 300 ml flaks, 20 g of 1,1-dimethoxyethene, 0.1 g of tetrabutylammonium bromide, 80 g of a 48% aqueous potassium hydroxide solution and 40 g of hexane were mixed, cooled to 5° C. and stirred, and 32 g of dichlorofluoromethane was continuously fed thereto so that the reaction temperature would not exceed 10° C. After completion of feeding of dichlorofluoromethane, disappearance of 1,1-dim ethoxyethene was confirmed by gas chromatography, and then 40 g of distilled water was added to separate the reaction mixture into two layers. The content of 1-chloro-1-fluoro-2,2-dimethoxycyclopropane contained in the crude liquid was 29 g by $^1$H-NMR (quantitative determination by internal standard method). The yield was 83.6%.

$^1$H-NMR and $^{19}$F-NMR data of 1-chloro-1-fluoro-2,2-dimethoxycyclopropane are shown below.

$^1$H-NMR (400 MHz, CDCl$_3$), δ ppm; 1.51 (dd, 1H), 1.74 (dd, 1H), 3.47 (s, 3H), 3.49 (s, 3H).

$^{19}$F-NMR (400 MHz, CDCl$_3$), δ ppm; −147.35 (dd, 1F).

Further, the content of 2-fluoro-3,3,3-trimethoxy-1-propene was 1.7 g by $^1$H-NMR (quantitative determination by internal standard method). The yield was 5.0%.

$^1$H-NMR and $^{19}$F-NMR data of 2-fluoro-3,3,3-trimethoxy-1-propene are shown below.

$^1$H-NMR (400 MHz, CDCl$_3$), δ ppm; 3.22 (s, 9H), 5.22 (dd, 1H), 6.92 (dd, 1H).
$^{19}$F-NMR (400 MHz, CDCl$_3$), δ ppm; −126.09 (dd, 1F).

Example 8(Step (iii))

In a 100 ml three-necked flask connected with a receiver (cooled to 0° C., 0.5 g of 2,6-di-tert-butyl-4-methylphenol (BHT) as a polymerization inhibitor initially added) for reaction distillation, 0.5 g of 2,6-di-tert-butyl-4-methylphenol (BHT) and 100 ml of 1,2,4-trichlorobenzene are put, and the pressure is reduced to a degree of vacuum of 360 torr. The flask is heated to 145° C., dropwise addition of 45 g of the organic layer crude liquid prepared in Example 7 is started, and dropwise addition is continued at a rate to maintain the internal temperature of 145° C. Formed methyl α-fluoroacrylate is collected in the receiver. The content of methyl α-fluoroacrylate contained in the crude liquid collected in the receiver is 10 g by $^1$H-NMR (quantitative determination by internal standard method). The yield is 94.6%.

The method for producing a halogenated acrylic acid derivative of the present invention is a method for producing a halogenated acrylic acid derivative as a final product with a high conversion ratio, a high selectivity and a high yield from an easily available orthocarboxylic acid derivative as a material, and is industrially very useful. Further, intermediates and final products produced by the method for producing a halogenated acrylic acid derivative of the present invention are compounds useful as an intermediate of pharmaceutical agents, polymers, etc.

The entire disclosure of Japanese Patent Application No. 2015-168339 filed on Aug. 27, 2015 including specification, claims and summary is incorporated herein by reference in its entirety.

What is claimed is:

1. A method for producing a halogenated acrylic acid ester compound, comprising:

subjecting a compound of formula (1) having a boiling point of at most 500° C. to R$^3$OH removal reaction in a vapor phase in the presence of a solid catalyst which is at least one solid catalyst selected from the group consisting of a metal catalyst and a metal oxide catalyst to produce an ethene compound of formula (2), wherein the R$^3$OH removal reaction is conducted by flowing a vaporized compound of formula (1) through a catalyst layer which comprises the solid catalyst:

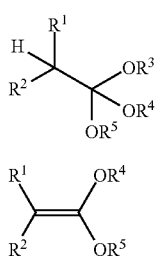

wherein each of R1 and R2 is independently a hydrogen atom, an alkyl group, a cycloalkyl group, an alkoxy group, an aryl group, an aryloxy group, an alkyl group having a substituent, a cycloalkyl group having a substituent, an alkoxy group having a substituent, an aryl group having a substituent, or an aryloxy group having a substituent, and each of R3, R4 and R5 is independently an alkyl group, a cycloalkyl group, an aryl group, an alkyl group having a substituent, a cycloalkyl group having a substituent, or an aryl group having a substituent;

reacting the ethene compound of formula (2) and a compound of formula (3) in the presence of a basic compound and a phase transfer catalyst which is at least one selected from the group consisting of a tetrabutylammonium salt, a trioctylmethylammonium salt and a benzyldimethyloctadecylammonium salt to produce a cyclopropane compound of formula (4):

wherein each of X, Y and Z is independently a halogen atom, and R$^1$, R$^2$, R$^4$ and R$^5$ are each as defined in formula (1); and subjecting the cyclopropane compound of formula (4) to R$^4$Y removal reaction by heating the cyclopropane compound of formula (4) in a liquid phase or in a vapor phase to produce a halogenated acrylic acid ester compound of formula (5):

wherein R$^1$, R$^2$ and R$^5$ are each as defined in formula (1), and X is as defined in formula (4).

2. The according to claim 1, wherein X is a fluorine atom.

3. The method according to claim 1, wherein the temperature of the R$^4$Y removal reaction is from 80 to 400° C.

4. The method according to claim 1, wherein production of the halogenated acrylic acid ester compound of formula (5) is carried out in the presence of a polymerization inhibitor.

5. The method according to claim 4, wherein the amount of the polymerization inhibitor is at least 10 ppm based on the halogenated acrylic acid ester compound.

6. The method according to claim 1, wherein a temperature of the R$^3$OH removal reaction is from 100 to 500° C.

7. The method according to claim 1, wherein the solid catalyst is a metal oxide catalyst.

8. The method according to claim 7, wherein the metal oxide catalyst comprises at least one member selected from the group consisting of zirconia, alumina, zeolite and zinc oxide.

9. The method according to claim 1, wherein the basic compound is at least one member selected from the group consisting of an alkali metal hydroxide, an alkali metal alkoxide, an alkali metal hydride and an alkyllithium.

10. The method according to claim 1, wherein X is a fluorine atom, and Y is a chlorine atom or a fluorine atom.

11. The method according to claim 7, wherein the metal oxide catalyst comprises zinc oxide.

\* \* \* \* \*